United States Patent
Kosuda

(10) Patent No.: US 7,144,375 B2
(45) Date of Patent: Dec. 5, 2006

(54) PULSIMETER, CONTROL METHOD FOR PULSIMETER, WRISTWATCH INFORMATION DEVICE, CONTROL PROGRAM, AND RECORDING MEDIUM

(75) Inventor: Tsukasa Kosuda, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 564 days.

(21) Appl. No.: 10/654,257

(22) Filed: Sep. 3, 2003

(65) Prior Publication Data

US 2004/0106872 A1    Jun. 3, 2004

(30) Foreign Application Priority Data

Sep. 6, 2002    (JP)    ............... 2002-261412

(51) Int. Cl.
*A61B 5/00*    (2006.01)
(52) U.S. Cl. ...................... 600/503; 600/500
(58) Field of Classification Search .............. None
See application file for complete search history.

(56) References Cited

U.S. PATENT DOCUMENTS 6,491,647 B1 *  12/2002  Bridger et al. ............... 600/585
6,529,754 B1 *   3/2003  Kondo ........................ 600/344

FOREIGN PATENT DOCUMENTS

JP    2816944    8/1998

* cited by examiner

*Primary Examiner*—Robert L. Nasser
*Assistant Examiner*—Karen E Toth
(74) *Attorney, Agent, or Firm*—Rosalio Haro

(57) ABSTRACT

A frequency analyzer carries out a frequency analysis on a pulse wave signal output from a pulse wave detector. A candidate extractor extracts candidate spectrum peaks from a frequency analysis result of the frequency analyzer. A phase variation calculator calculates variations in phase angle of each of the extracted candidate spectrum peaks, and a spectrum peak selector selects a target spectrum peak from among the extracted candidate spectrum peaks based on their respective variations in phase angle. A pulse rate is calculated using the target spectrum peak.

18 Claims, 12 Drawing Sheets

| Condition whether pure pulse wave and body motion wave overlap | Variation Δσ in phase angle of the harmonic of the composite signal that corresponds to the first higher harmonic of the body motion signal | Variation Δσ in phase angle of the harmonic of the composite signal that corresponds to the second higher harmonic of the body motion signal |
|---|---|---|
| A  No overlap | 13.2° | 16.8° |
| B  Pure pulse wave overlap with first higher harmonic of body motion signal | 62.8° : Phase angle variation is high | 16.2° |
| C  Pure pulse wave overlap with second higher harmonic of body motion | 12.9° | 46.2° : Phase angle variation is high |

FIG. 8

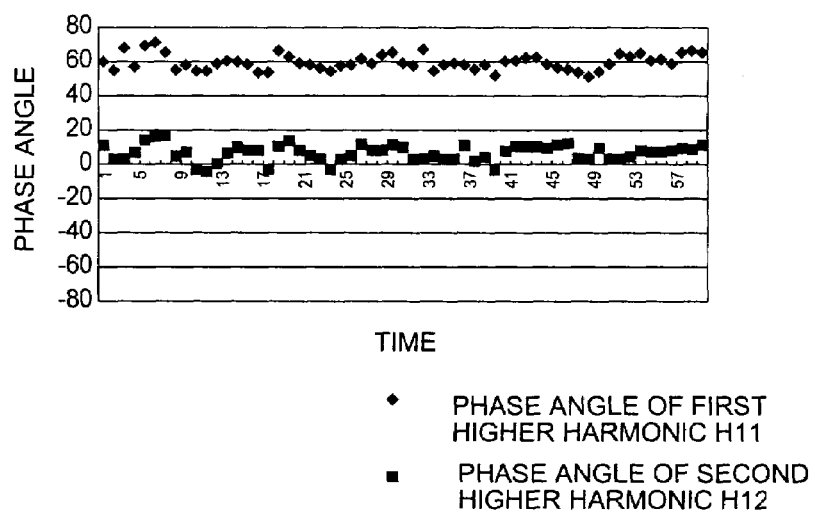

◆  PHASE ANGLE OF FIRST HIGHER HARMONIC H11

■  PHASE ANGLE OF SECOND HIGHER HARMONIC H12

FIG. 9

PULSIMETER, CONTROL METHOD FOR PULSIMETER, WRISTWATCH INFORMATION DEVICE, CONTROL PROGRAM, AND RECORDING MEDIUM

BACKGROUND OF THE INVENTION

1. Field of the Invention

The present invention relates to a pulsimeter, a control method for a pulsimeter, a control program and a recording medium, and more particularly, it relates to a pulsimeter attached to a part of a human body to measure a pulse rate while walking or running, a control method for a pulsimeter, a control program and a recording medium.

2. Description of the Related Art

Hitherto, there has been known a sphygmograph attached to a part of a human body to measure pulses while walking or running.

For example, Japanese patent No. 2816944 discloses such a wrist pulsimeter. This pulsimeter attempts to remove body motion harmonic components from a pulse wave signal prior to determining the pulse rate from the pulse wave signal. That is, the pulsimeter is constructed to conduct frequency analysis on a body motion signal to identify body motion harmonics, and then to remove all higher body motion harmonic components from a frequency analysis of a pulse wave signal. Then from among the remaining pulse wave frequency components, the frequency component having highest power is extracted, and a pulse rate is calculated based on the extracted frequency component. Therefore, in this conventional pulsimeter, if a pulse wave component overlaps a body motion component, then the overlapping pulse wave component is inadvertently also removed when the body motion component is removed. Since this distorts the pulse wave signal, it prevents the accurate calculation of a pulse rate.

A case where a pulse wave component overlaps a body motion component is specifically referred to as a case where a pulse rate equals a motion pitch. In general, a walking (motion) pitch ranges from 100 to 120, and coincidentally, the pulse rate during walking frequently also ranges from about 100 to about 120. Thus, during walking, pulse wave components frequently overlap body motion components, although there are individual variations.

OBJECTS OF THE INVENTION

Accordingly, an object of the present invention is to provide a pulsimeter that allows pulse rates to be accurately calculated even if body motion components overlap pulse wave components.

A second object of the present invention is to provide a control method for a pulsimeter, a control program for controlling a pulsimeter, and a recording medium having a control program to allow pulse rates to be accurately calculated even if body motion components overlap pulse wave components.

SUMMARY OF THE INVENTION

To solve the aforesaid problem, a pulsimeter in accord with the present invention is provided with a pulse wave detector that has a pulse wave sensor and outputs a pulse wave signal, a frequency analyzer for carrying out a frequency analysis on the pulse wave signal, a candidate extractor for extracting candidate frequency components from the frequency analysis result of the frequency analyzer, a phase angle information detector for determining phase angle information of each extracted candidate frequency component, a calculation object determiner for selecting (basis of the phase angle information) a candidate frequency component from which to calculate a pulse rate, and a pulse rate calculator for calculating the pulse rate based on the selected candidate frequency component.

With this arrangement, the frequency analyzer carries out a frequency analysis on a pulse wave signal output from the pulse wave detector.

The candidate extractor extracts candidate frequency components from the spectrum resulting from the frequency analysis.

The phase angle information detector determines the phase angle information of each of the extracted candidate frequency components.

Based on the above phase angle information, the calculation object determiner selects (i.e. identifies) a candidate frequency component from which to calculate a pulse rate. The pulse rate calculator then calculates the pulse rate based on the selected candidate frequency component.

In this case, the phase angle information may include information regarding variations in phase angle or variations in phase angle difference per unit time, and the calculation object determiner may select the candidate frequency component exhibiting the greatest variation in phase angle, or the greatest variation in phase angle difference per unit time, among all the candidate frequency components as the candidate frequency component upon which to calculate the pulse rate.

A pulsimeter in accord with the present invention has a pulse wave detector that has a pulse wave sensor and outputs a pulse wave signal, and a body motion detector that has a body motion sensor and outputs a body motion signal. It is to be understood that the pulse wave signal produced by the pulse wave sensor will inherently include body motion frequency components if the person wearing the present pulsimeter is active during the reading of his/her pulse rate. To discriminate the body motion components from the pure pulse wave components, the present invention further includes a frequency analyzer for analyzing both the observed pulse wave signal and the body motion signal, a candidate extractor for extracting candidate frequency components from the frequency analysis of the pulse wave signal, a candidate identifier for identifying (i.e. selecting) a particular candidate frequency component from among the plurality of candidate pulse wave frequency components, a first calculation object determiner for determining whether the pulse wave deriving candidate spectra have a first spectrum, which is a characteristic spectrum that can be a pulse rate calculation object, a phase angle information detector for detecting phase angle information, which is the information regarding phase angles, on each of the extracted candidate spectra corresponding to the pulse wave signal if the first spectrum does not exist, a second calculation object determiner for determining a second spectrum, which is a characteristic spectrum of a pulse rate calculation object, among the candidate spectra on the basis of the phase angle information, and a pulse rate calculator for calculating a pulse rate on the basis of either the first spectrum or the second spectrum.

With this arrangement, the pulse wave detector outputs a pulse wave signal to the frequency analyzer. Meanwhile, the body motion detector outputs a body motion signal to the frequency analyzer.

The frequency analyzer carries out a frequency analysis on each of the pulse wave signal and the body motion signal, and the candidate extrator extracts candidate spectra corresponding to the pulse wave signal and the body motion signal, respectively, on the basis of the result of the frequency analysis.

The candidate identifier identifies a pulse wave deriving candidate spectrum, which is a candidate spectrum deriving from a pulse wave, among the candidate spectra corresponding to the pulse wave signal and the body motion signal, respectively.

The first calculation object determiner determines whether the pulse wave deriving candidate spectra have a first spectrum, which is a characteristic spectrum that can be a pulse rate calculation object.

The phase angle information detector detects phase angle information, which is the information regarding phase angles, on each of the extracted candidate spectra corresponding to the pulse wave signal if the first spectrum does not exist.

The second calculation object determiner determines a second spectrum, which is a characteristic spectrum of a pulse rate calculation object, among the candidate spectra on the basis of the phase angle information.

The pulse rate calculator for calculating a pulse rate on the basis of either the first spectrum or the second spectrum.

In this case, the phase angle information may include information regarding variations in phase angle or variations in phase angle difference per unit time between phase angles of the extracted candidate spectra corresponding to the body motion signal and phase angles of the extracted candidate spectra corresponding to the pulse wave signal, and the second calculation object determiner may take the candidate spectrum exhibiting a greatest variation in phase angle or a greatest variation in phase angle difference per unit time among the candidate spectra as the second spectrum.

A control method for a pulsimeter provided with a pulse wave detector that has a pulse wave sensor and outputs a pulse wave signal is characterized by including a frequency analysis step for carrying out a frequency analysis on the pulse wave signal, a candidate extraction step for extracting candidate spectra from a result of the frequency analysis, a phase angle information detection step for detecting phase angle information, which is the information regarding phase angles, on each of the candidate spectra that have been extracted, a calculation object determination step for determining a candidate spectrum for calculating a pulse rate among the candidate spectra on the basis of the phase angle information, and a pulse rate calculation step for calculating a pulse rate on the basis of the candidate spectrum for calculating the pulse rate.

In this case, the phase angle information may include information regarding variations in phase angle or variations in phase angle difference per unit time, and the calculation object determination step may take the candidate spectrum exhibiting a greatest variation in phase angle or a greatest variation in phase angle difference per unit time among the candidate spectra as the candidate spectrum for calculating the pulse rate.

A control method for a pulsimeter provided with a pulse wave detector that has a pulse wave sensor and outputs a pulse wave signal and a body motion detector that has a body motion sensor and outputs a body motion signal is characterized by including a frequency analysis step for carrying out a frequency analysis on each of the pulse wave signal and the body motion signal, a candidate extraction step for extracting candidate spectra corresponding to the pulse wave signal and the body motion signal from a result of the frequency analysis, a candidate identification step for identifying a pulse wave deriving candidate spectrum, which is a candidate spectrum deriving from a pulse wave, among the candidate spectra corresponding to the pulse wave signal and the body motion signal, respectively, a first calculation object determination step for determining whether the pulse wave deriving candidate spectra have a first spectrum, which is a characteristic spectrum that can be a pulse rate calculation object, a phase angle information detection step for detecting phase angle information, which is the information regarding phase angles, on each of the extracted candidate spectra corresponding to the pulse wave signal if the first spectrum does not exist, a second calculation object determination step for determining a second spectrum, which is a characteristic spectrum of a pulse rate calculation object, among the candidate spectra on the basis of the phase angle information, and a pulse rate calculation step for calculating a pulse rate on the basis of either the first spectrum or the second spectrum.

In this case, the phase angle information may include information regarding variations in phase angle or variations in phase angle difference per unit time between phase angles of the extracted candidate spectra corresponding to the body motion signal and phase angles of the extracted candidate spectra corresponding to the pulse wave signal, and the second calculation object determination step may take the candidate spectrum exhibiting a greatest variation in phase angle or a greatest variation in phase angle difference per unit time among the candidate spectra as the second spectrum.

A wristwatch information device that is attached to a pulse wave detection position of a body, and provided with a pulse wave detector that has a pulse wave sensor and outputs a pulse wave signal and a main unit to be attached to an arm, is characterized in that the main unit includes a frequency analyzer for carrying out a frequency analysis on the pulse wave signal, a candidate extractor for extracting candidate spectra from a frequency analysis result in the frequency analyzer, a phase angle information detector for detecting phase angle information, which is the information regarding phase angles, on each of the candidate spectra that have been extracted, a calculation object determiner for determining a candidate spectrum for calculating a pulse rate among the candidate spectra on the basis of the phase angle information, a pulse rate calculator for calculating a pulse rate on the basis of the candidate spectrum for calculating the pulse rate, and a display unit for displaying the pulse rate.

A wristwatch information device that is to be attached to a pulse wave detection position of a body, and is provided with a pulse wave detector that has a pulse wave sensor and outputs a pulse wave signal and a main unit to be attached to an arm, is characterized in that the main unit includes a body motion detector that has a body motion sensor and outputs a body motion signal, a frequency analyzer for carrying out a frequency analysis on each of the pulse wave signal and the body motion signal, a candidate extractor for extracting candidate spectra corresponding to the pulse wave signal and the body motion signal from a frequency analysis result in the frequency analyzer, a candidate identifier for identifying a pulse wave deriving candidate spectrum, which is a candidate spectrum deriving from a pulse wave, among the candidate spectra corresponding to the pulse wave signal and the body motion signal, respectively, a first calculation object determiner for determining whether the pulse wave deriving candidate spectra have a first spectrum, which is a characteristic spectrum that can be a pulse rate calculation object, a phase angle information detector for detecting phase angle information, which is the information regarding phase angles, on each of the extracted candidate spectra corresponding to the pulse wave signal if the first spectrum does not exist, a second calculation object determiner for determining a second spectrum, which is a characteristic spectrum of a pulse rate calculation object from the candidate spectra on the basis of the phase angle information, a pulse rate calculator for calculating a pulse rate on the basis of either the first spectrum or the second spectrum, and a display unit for displaying the pulse rate.

A control program for controlling, by a computer, a pulsimeter equipped with a pulse wave detector that has a pulse wave sensor and outputs a pulse wave signal is characterized in that it causes a frequency analysis to be performed on the pulse wave signal, candidate spectra to be extracted from a result of the frequency analysis, phase angle information, which is information regarding phase angles, to be detected on each of the candidate spectra that have been extracted, a candidate spectrum for calculating a pulse rate to be determined among the candidate spectra on the basis of the phase angle information, and a pulse rate to be calculated on the basis of the candidate spectrum for calculating the pulse rate.

A control program for controlling, by a computer, a pulsimeter provided with a pulse wave detector that has a pulse wave sensor and outputs a pulse wave signal and a body motion detector that has a body motion sensor and outputs a body motion signal is characterized in that it causes a frequency analysis to be performed on each of the pulse wave signal and the body motion signal, candidate spectra corresponding to the pulse wave signal and the body motion signal, respectively, to be extracted from a result of the frequency analysis, a pulse wave deriving candidate spectrum, which is a candidate spectrum deriving from a pulse wave, to be identified among the candidate spectra corresponding to the pulse wave signal and the body motion signal, respectively, whether the pulse wave deriving candidate spectra have a first spectrum, which is a characteristic spectrum that can be a pulse rate calculation object, to be determined, phase angle information, which is the information regarding phase angles, to be detected on each of the extracted candidate spectra corresponding to the pulse wave signal if the first spectrum does not exist, a second spectrum, which is a characteristic spectrum of a pulse rate calculation object, to be determined from the candidate spectra on the basis of the phase angle information, and a pulse rate to be calculated on the basis of either the first spectrum or the second spectrum.

Furthermore, the aforesaid control program may be recorded in a computer-readable recording medium.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIG. 8 is a table of exemplary phase angle values for peaks in the frequency spectrum of a composite (i.e. observed) pulse wave that correspond to a first and second higher harmonic of a body motion signal under three conditions: (1) when the frequency component of the pure pulse signal does not overlap any motion signal frequency components; (2) the frequency component of the pure pulse signal overlaps the first higher harmonic of the motion signal; and (3) the frequency component of the pure pulse signal overlaps the second higher harmonic of the motion signal.

FIG. 9 is an explanatory diagram of case A in FIG. 8 showing measurement results temporal changes in phase angles of spectrum peaks of the composite signal that correspond to the first H11 and second H12 spectrum peaks of the body motion signal shown in FIG. 7a.

DESCRIPTION OF THE PREFERRED EMBODIMENTS

Preferred embodiments of the present invention will be explained with reference to the accompanying drawings.

[1] First Embodiment

Figure 1:
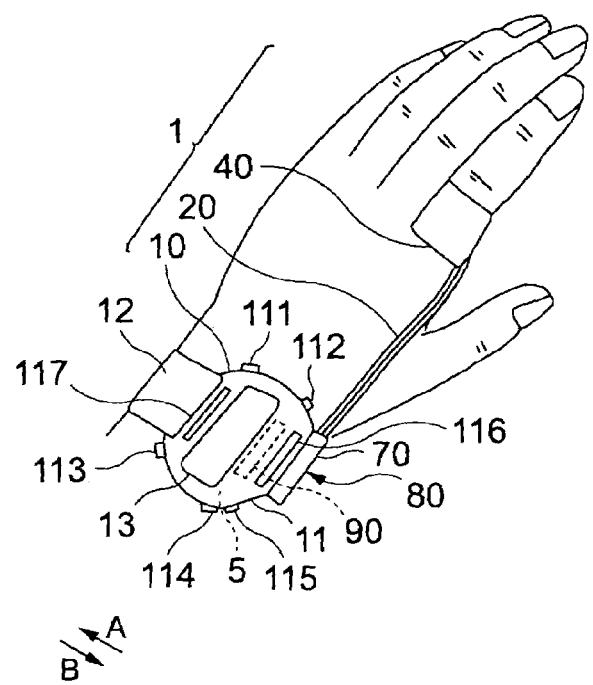
FIG. 1 is top-view of a wristwatch information device according to an embodiment of the present invention.

With reference to FIG. 1, wristwatch information device 1 is primarily constructed of a main body unit 10 preferably having a wristwatch shape, a cable 20 connected to main body unit 10, and a pulse wave sensor 30 provided at the distal end of the cable 20.

A connector piece 80 is formed on one end of the cable 20. The connector piece 80 is detachably installed onto a connector 70 preferably provided on the side of main unit 10 adjacent the 6 o'clock position.

Main unit 10 is provided with a wristband 12 for winding around an arm (or wrist). Preferably wristband 12 winds around from a first fixed location at the 12 o'clock position of a wristwatch to a second fixed location at the 6 o'clock position. Main unit 10 is detachably mounted on the arm by means of this wristband 12.

Figure 2:
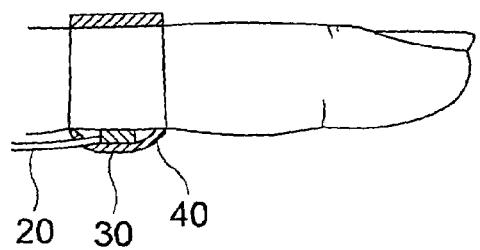
FIG. 2 is a close-up view of the pulse wave sensor of the wristwatch information device shown in FIG. 1.

With reference to FIG. 2, pulse wave sensor 30 is preferably positioned between the base and knuckle joint of a forefinger. Pulse wave sensor 30 is shielded from light by a sensor fixing band 40. Thus, since pulse wave sensor 30 is positioned at the base of the finger, the length of cable 20 can be made short, so that cable 20 does not interfere with running or other physical activity. Measurements of body temperature distribution from the palm to fingertips indicate that in cold weather the temperatures of the fingertips significantly drop, whereas the temperatures at the base of the fingers do not relatively drop. Hence, by installing the pulse wave sensor 30 at the base of a finger, a pulse rate (or the like) can be accurately measured even when a person wearing the device runs outdoors on a cold day.

Figure 3:
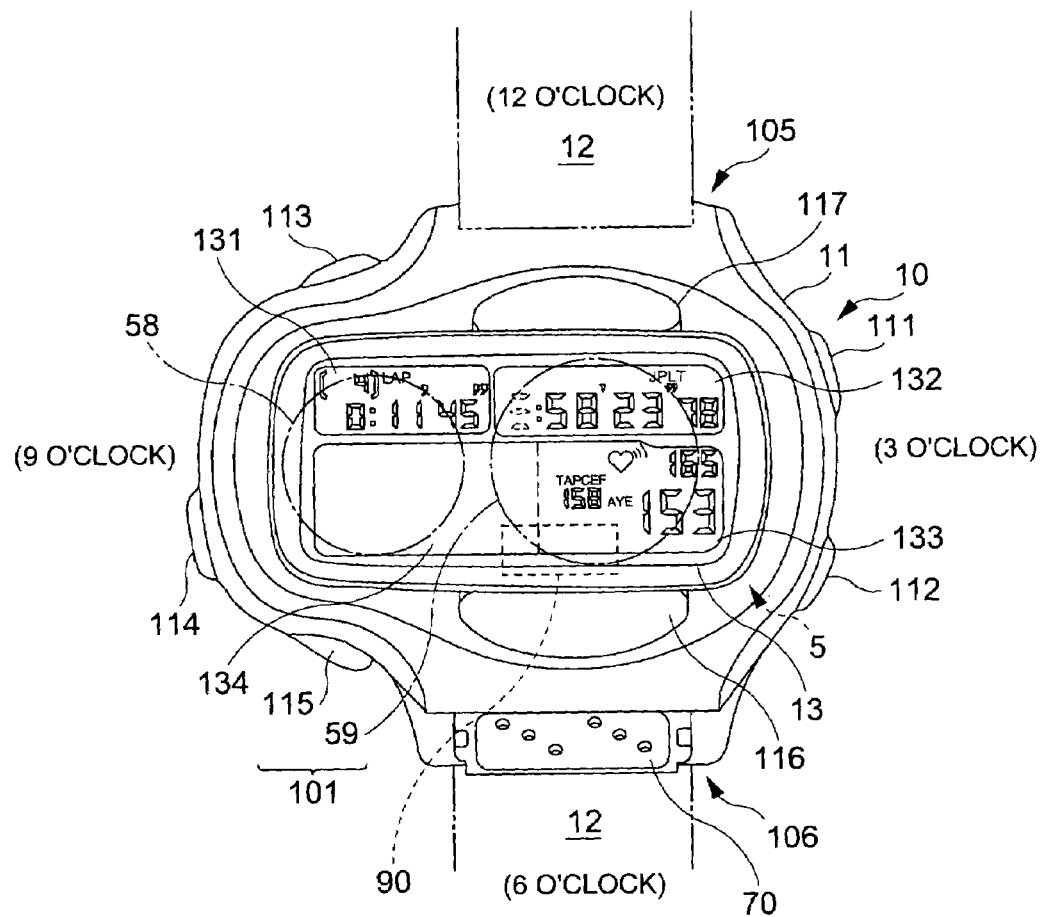
FIG. 3 is a top plan view of the main unit of the wristwatch information device shown in FIG. 1.
Figure 4:
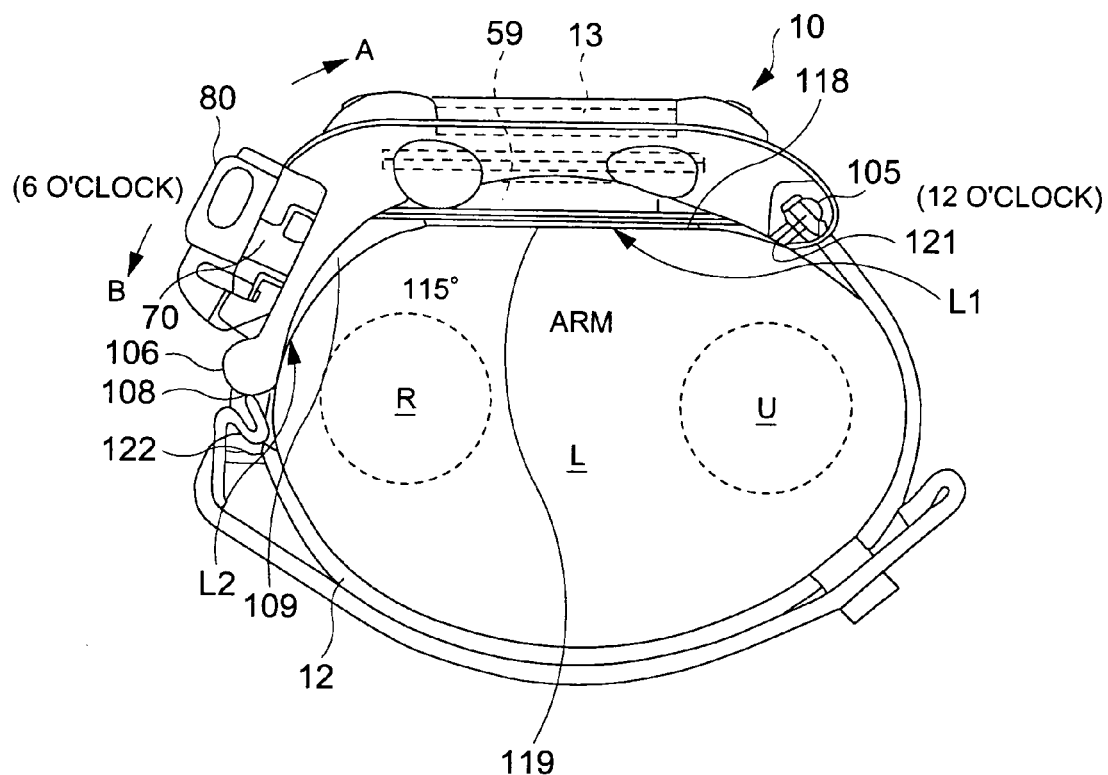
FIG. 4 is an explanatory diagram of the main unit of the wristwatch information device shown in FIG. 1, as observed from the 3 o'clock side of the wristwatch.

FIG. 3 is a top plan view of main unit 10 of wristwatch information device 1 with wristband 12 partially shown and cable 20 of FIGS. 1 and 2 not shown. FIG. 4 is a side view of wristwatch information device 1 observed from its 3 o'clock direction.

In FIG. 3, main unit 10 is equipped with a resinous watchcase 11 (main unit case). The front surface of watchcase 11 is provided with a liquid crystal display unit 13 (display unit) with an EL backlight that displays running or walking pitches and pulse wave information, such as a pulse rate, in addition to the current time and date.

Liquid crystal display unit 13 has a first segment display region 131 at the top left position of a display surface, a second segment display region 132 at the top right position, a third segment display region 133 at bottom the right position, and a dot display region 134 at the bottom left position. Various types of information can be graphically displayed within dot display region 134.

A body motion sensor 302 for determining motion pitches (refer to FIG. 6) is built within watchcase 11. Body motion sensor 302 can be implemented using an acceleration sensor, or similar device.

Furthermore, a controller 5 for carrying out various types of control and data processing is provided within watchcase 11. Pitches are determined by controller 5 on the basis of motion detection results (body motion signals) supplied by body motion sensor 302 and displayed on liquid crystal display unit 13. Controller 5 also determines changes in pulse rate, or the like, on the basis of pulse detection results (pulse wave signals) supplied by pulse wave sensor 30, and causes liquid crystal display unit 13 to display the determined changes in pulse rate, or the like.

In this case, controller 5 also includes a time circuit, so that regular time, lap time, split time, etc. can be displayed on liquid crystal display unit 13.

Button switches 111 through 115 for performing external operations, such as time adjustment or display mode changeover, are provided on the outer peripheral portion of watchcase 11. The front surface of the watchcase has large button switches 116 and 117.

The power source of wristwatch information device 1 is formed of a button-shaped small battery 59 housed within watchcase 11. Power is supplied from battery 59 to pulse wave sensor 30 through cable 20. The detection results of pulse wave sensor 30 are supplied to controller 5 of watchcase 11.

Main unit 10 of wristwatch information device 1 must be made larger as the number of features is expanded. However, main unit 10 has dimension restrictions since it is worn on an arm. Therefore, the size of main unit 10 cannot be increased in the customary 6 o'clock direction or 12 o'clock direction of an analog wristwatch.

According to the present embodiment, therefore, the main unit 10 forms a horizontally elongated watchcase 11, in which its length in the 3 o'clock and 9 o'clock directions is greater than its length in the 6 o'clock and 12 o'clock directions.

In this case, wristband 12 is preferably connected at a position shifted toward the 3 o'clock side. As observed from the wristband, a protuberant portion 101 is provided on the customary 9 o'clock side of an analog wristwatch, while no such protuberant portion is provided on the 3 o'clock side. Accordingly, watchcase 11, although horizontally long, allows the wearer to freely bend his or her wrist and also protects the back of his or her hand from hitting against watchcase 11 if he or she stumbles.

Inside watchcase 11, a flat piezoelectric element 58 functions as a buzzer and is positioned along the 9 o'clock side in relation to battery 59. Battery 59 is heavier than the piezoelectric element 58, so that the center of gravity of main unit 10 is shifted toward the 3 o'clock side. Wristband 12 is connected to the side where the center of gravity is located, making it possible to securely attach main unit 10 to an arm. Moreover, battery 59 and piezoelectric element 58 are preferably disposed along the same plane, so that main unit 10 can be made thinner. In addition, as shown in FIG. 4, a battery cover 118 is provided on a back surface 119, enabling a user to easily replace battery 59.

In FIG. 4, a coupling 105 for retaining a lock shaft 121 installed at an end of wristband 12 is formed at the 12 o'clock side of watchcase 11. At the 6 o'clock side of watchcase 11, wristband 12, which would wrap around an arm, is folded back to a middle position of its length. A receiver 106, to which a retainer 122 for holding the middle position is installed, is also formed at the 6 o'clock side.

At the 6 o'clock side of main unit 10, a rotation stopper 108 oriented at an angle of about 115° in relation to back surface 119 is formed integrally with watchcase 11, extending from back surface 119 to receiver 106. This means that, if main unit 10 is attached using wristband 12 such that it is positioned on an upper surface L1 (adjacent to the back of the hand) of a left wrist L (arm), then back surface 119 of watchcase 11 is brought into close contact with upper surface L1 of wrist L. At the same time, rotation stopper 108 abuts against a side surface L2 adjacent to a radius R.

Under this condition, back surface 119 of main unit 10 extends over the radius R and the ulna U bone of the arm. At the same time, the portion that extends from a curved portion 109 between the rotation stopper 108 and the back surface 119 to the rotation stopper 108 is in contact with the radius R. Thus, the angle formed by the rotation stopper 108 and the back surface 119 is set to about 115°, which is anatomically ideal. Therefore, even if a force is applied to cause main unit 10 to be rotationally shifted in the direction indicated by arrow A or B, main unit 10 will not be easily dislocated around the arm L.

The rotational dislocation of main unit 10 is restricted only at two points on one side around the arm by back surface 119 and rotation stopper 108. Hence, even if the arm is thin, back surface 119 and rotation stopper 108 will securely come in contact with the arm, ensuring achievement of the rotation stopping effect. Furthermore, even if the wearer has a thick arm, the main unit 10 will not feel tight to the wearer.

Figure 5:
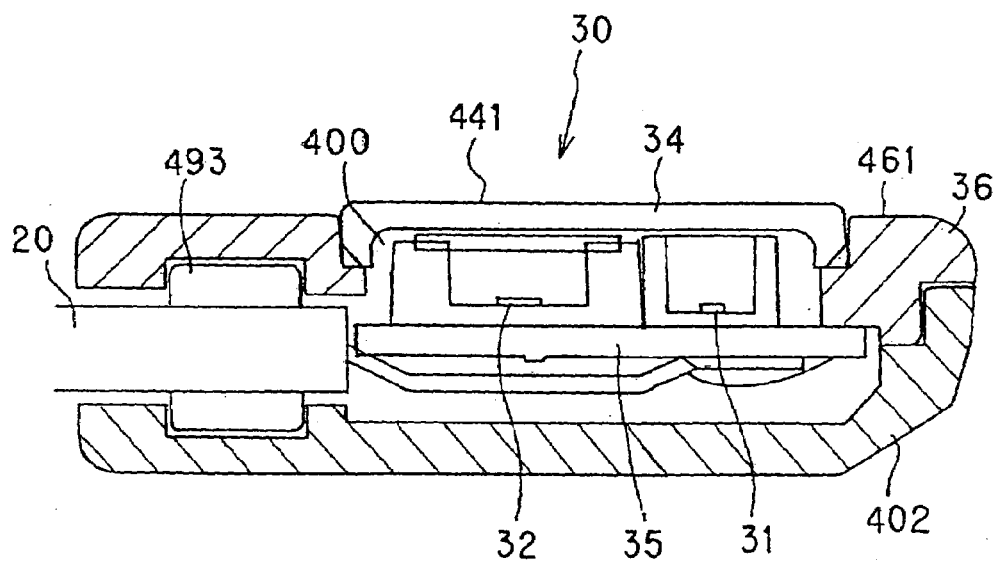
FIG. 5 is a sectional view of the pulse wave sensor used with the wristwatch information device shown in FIG. 1.

FIG. 5 is a sectional view of pulse wave sensor 30 according to the present embodiment.

In FIG. 5, pulse wave sensor 30 has a parts accommodating space 400 formed by a rear cover 402 provided on the rear side of a sensor frame 36 serving as the casing of pulse wave sensor 30. A circuit board 35 is disposed in the parts accommodating space 400. Mounted on the circuit board 35 are an LED 31, a phototransistor 32 and other electronic components. An end of cable 20 is fixed to pulse wave sensor 30 by a bushing 493, and each wire of cable 20 is soldered onto specific lead patterns on circuit board 35. Pulse wave sensor 30 is attached to a finger such that cable 20 is drawn from the base of the finger toward main unit 10. Hence, LED 31 and phototransistor 32 are positioned at the base of the finger, but arranged along the length of the finger. Preferably, LED 31 is positioned closer to the fingertip, while phototransistor 32 is positioned closer to the palm. This arrangement is advantageously effective for preventing external light from reaching the phototransistor 32.

The pulse wave sensor 30 has a light transmitting window that is formed of a translucent plate 34 made of glass and disposed in the upper surface (substantially the detecting portion for pulse wave signals) of sensor frame 36. LED 31 directs its light emitting surface toward translucent plate 34, and the phototransistor 32 directs its light receiving surfaces toward translucent plate 34. Therefore, when the surface of a finger is set in close contact with an outer surface 441 (the surface of pulse wave sensor 30 in contact with the finger surface) of translucent plate 34, LED 31 emits light toward the finger surface. This sets phototransistor 32 ready to receive LED transmitted light that is reflected back from the finger. In order to enhance the close contact between outer surface 441 of translucent plate 34 and the finger surface, outer surface 441 of translucent plate 34 protrudes from a surrounding portion 461 thereof.

In this embodiment, an InGaN type (indium-gallium-nitrogen type) blue LED is used as LED 31, the light emission spectrum thereof having its emission peak at 450 nm. The light emission wavelengths of LED 31 range from 350 nm to 600 nm. For LED 31 having such light emission characteristics, a GaAsP type (gallium-arsenic-phosphorus type) phototransistor is used as phototransistor 32 (i.e. photodetector) in this embodiment. Regarding the light receiving wavelength range of phototransistor 32, the major sensitivity ranges from 300 nm to 600 nm, and there is also a sensitivity range below 300 nm.

Pulse wave sensor 30, constructed as described above, is attached to the base of a finger by sensor fixing band 40, and light is irradiated from LED 31 to the finger in that state, the light reaches a blood vessel and a part of the light is absorbed by the hemoglobin in the blood, while a part of the light is reflected. The light reflected from the finger (blood vessel) is received by phototransistor 32, and changes in the amount of received light correspond to changes in the amount of blood (pulse waves of the blood). More specifically, the intensity of reflected light decreases as the amount of blood increases, while the intensity of reflected light increases as the amount of blood decreases, so that pulse rates, or the like, can be measured by detecting changes in the intensity of reflected light.

In this embodiment, biological information is displayed on the basis of detection results in the wavelength range from about 300 nm to about 600 nm in which the emission wavelength range of LED 31 and the light-intercepting wavelength range of phototransistor 32 overlap, namely, the wavelength range of about 700 nm or less.

Such a construction is taken because, even if external light hits an exposed portion of a finger, the light in the wavelength range of 700 nm or less among the light contained in the external ambient light does not reach the phototransistor 32 (light receiving portion) by using the finger as a photoconductor. This is because of the tendency in that it is difficult for the light having a wavelength range of 700 nm or less that is contained in external light to pass though a finger. For this reason, even when external light is irradiated at a finger portion not covered by sensor fixing band 40, the light does not pass through the finger and reach phototransistor 32, thereby not affecting measurement results.

If, however, an LED having its emission peak at around 880 nm and a silicon type phototransistor, for example, are used, then their light receiving wavelength range will be 350 nm to 1200 nm. In this case, pulse waves will be detected on the basis of detection results of light having a wavelength of 1 μm that easily reaches the light receiver using a finger as a photoconductor. This causes erroneous detections attributable to changes in external light to easily happen.

Furthermore, since the light in the wavelength range of about 700 nm or less is used to obtain pulse wave information, the SIN ratio of pulse wave signals based on changes in the amount of blood is high. This is considered to be due to the light absorbing coefficient of hemoglobin in blood, that is a few times to about 100 times, or more, higher for the light of wavelengths of 300 nm to 700 nm than the light having a wavelength of 880 nm, which is conventional detection light. It is regarded, therefore, that the light absorbing coefficient changes with high sensitivity to the changes in the amount of blood, resulting in a high detection rate (S/N ratio) of pulse waves based on the changes in the amount of blood.

Figure 6:
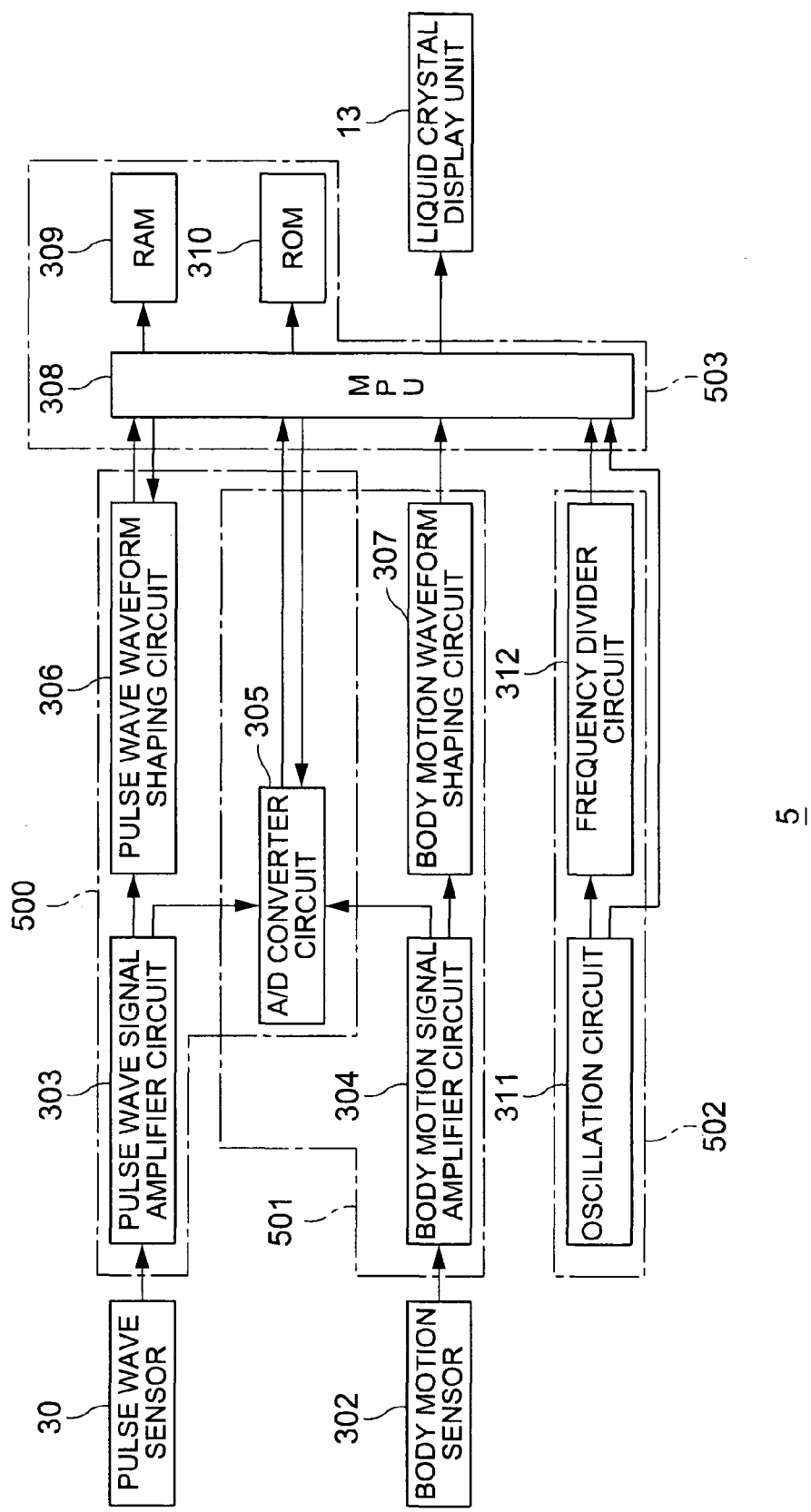
FIG. 6 is a block diagram showing a schematic configuration of a controller.

FIG. 6 is a block diagram showing the schematic configuration of controller 5.

Controller 5 is primarily constructed of a pulse wave data processor 500 for determining a pulse rate on the basis of an input result from pulse wave sensor 30, a pitch data processor 501 for determining a pitch on the basis of an input result from a body motion sensor 302, a clock generator 502 for generating operation clock signals, and a controller 503 for controlling the entire control system.

The pulse wave data processor 500 is primarily constructed of a pulse wave signal amplifier circuit 303 and a pulse wave waveform shaping circuit 306, and shares an A/D converting circuit 305 with pitch data processor 501.

Pulse wave signal amplifier circuit 303 amplifies pulse wave signals from pulse wave sensor 30, and outputs the amplified pulse wave signals to A/D converting circuit 305 and pulse wave waveform shaping circuit 306.

Pulse wave waveform shaping circuit 306 shapes the waveforms of the amplified pulse wave signals and outputs them to controller 503.

The A/D converting circuit 305 carries out A/D conversion on the amplified pulse wave signals and outputs them as pulse wave data to controller 503.

Pitch data processor 501 is primarily constructed of a body motion signal amplifier circuit 304 and a body motion waveform shaping circuit 307, and shares A/D converting circuit 305 with pulse wave data processor 500, as mentioned above.

Body motion signal amplifier circuit 304 amplifies body motion signals output from body motion sensor 302, and outputs the amplified body motion signals to A/D converting circuit 305 and body motion waveform shaping circuit 307.

Body motion waveform shaping circuit 307 shapes the waveforms of the amplified body motion signals and outputs the results to controller 503.

A/D converting circuit 305 carries out A/D conversion on the amplified body motion signals (i.e. digitizes the body motion signals) and outputs the results as body motion data to controller 503.

Clock generator 502 is primarily constructed of an oscillation circuit 311 and a frequency divider circuit 312.

Oscillation circuit 311 includes a crystal oscillator, or the like, and supplies clock signals as reference operation clocks to controller 503 and also to frequency divider circuit 312 to generate clocking signals from the clock signals.

Frequency divider circuit 312 divides supplied clock signals to generate various types of clocking signals and supplies the generated clocking signals to controller 503.

Controller 503 is primarily constructed of an MPU 308, a RAM 309 and a ROM 310.

MPU 308 controls the entire controller 5 and consequently the entire wristwatch information device 1 according to a control program stored in ROM 310.

RAM 309, which temporarily stores various types of data, including pulse wave data and body motion data, is used as a work area.

ROM 310 stores in advance a control program for controlling MPU 308 and consequently the entire wristwatch information device 1.

Before explaining a specific operation, the principle of the embodiment will be explained.

Frequency analysis of the body motion signals and pulse wave signals has shown that the phase angles of the waveforms remain constant as long as their frequencies are constant and their frequencies differ from each other.

However in real life, either one or both of the frequencies of the pure pulse wave signal and the body motion signal will fluctuate. That is, the frequencies will sometimes get separated and sometimes get closer and overlap. When they get closer and overlap, the phase angles of the composite signal become unstable and experience variation.

A reason for the phase angle variations of the composite signal will not be described.

If a pure pulse wave component and a body motion component overlap for an extended period of time, then the phase angles of the combined (i.e. overlapped) components should be constant without varying. However, in human motion, it is difficult to assume that a pulse rate and a motion pitch will remain constant when overlapping for an extended period of time. More characteristic of human behavior is to assume that waveforms of pulse waves and body motion waves may momentarily overlap to a varying degree and then separate. As waveforms (which individually have different phase angles) are overlapped and then separated, the amount of phase angle variation of the composite component (i.e. resultant from the two overlapping components) is increased. For example, if the phase angle of a frequency spectrum of a pure pulse wave component is 40° and the phase angle of the frequency spectrum of a body motion component is 100°, and if the pulse rate and the motion pitch get overlapped, or slightly misaligned, then the phase angle of the observed pulse wave component (which is the composite of the overlapping pure pulse wave component and the body motion component) will become unstable and vary sometimes by 40° and sometimes by 140°. In other words, since two frequency components having different phase angles overlap, the phase angle of the corresponding composite frequency component varies.

Accordingly, observing the amount of phase angle variation makes it possible to determine whether a pure pulse wave component and a body motion component are overlapped in an observed pulse wave, as produced by pulse wave sensor 30 of FIG. 6.

Figure 7A:
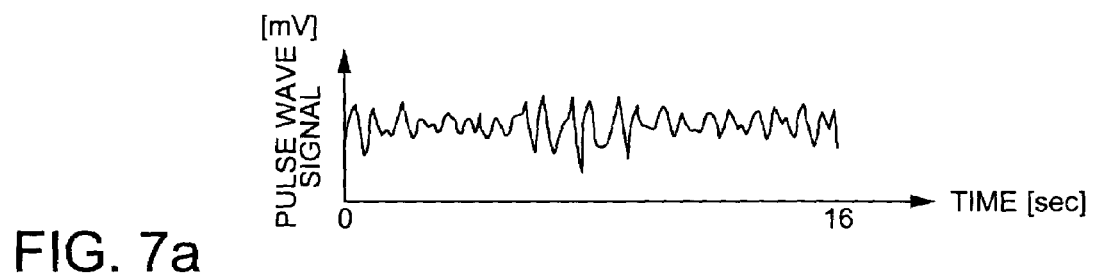
FIG. 7a is a first exemplary diagram of a pulse wave signal, such as might be observed by the pulse wave sensor of FIG. 6.
Figure 7B:
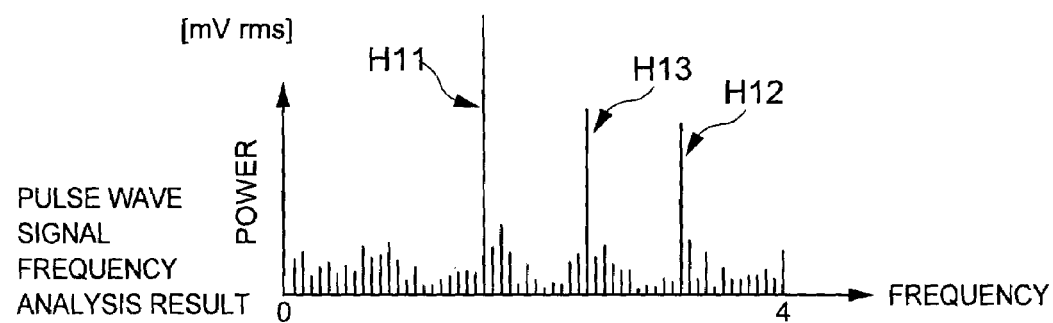
FIG. 7b is a spectrum diagram of the pulse wave signal of FIG. 7a, which includes both body motion harmonics and a pure pulse wave frequency component.

An example of an observed pulse wave in which its pure pulse wave component does not overlap any body motion components is illustrated in FIGS. 7a to 7d. More specifically, FIG. 7a shows an observed pulse wave signal, such as might be observed if the wearer of the pulsimeter is engaged in active motion. As shown in FIG. 7b, the frequency analysis (FFT) of the observed pulse wave signal of FIG. 7a indicates three spectrum peaks H11, H13, and H12. Presumably, at least one of these spectrum peaks corresponds to a harmonic of the pure pulse signal while the remainder correspond to body motion harmonics. To identify the harmonic corresponding to the pure pulse signal, one first analyzes the observed body motion signal and identifies its harmonics.

Figure 7C:
FIG. 7c is a first exemplary diagram of a body motion signal, such as might be observed by the body motion sensor of FIG. 6.
Figure 7D:
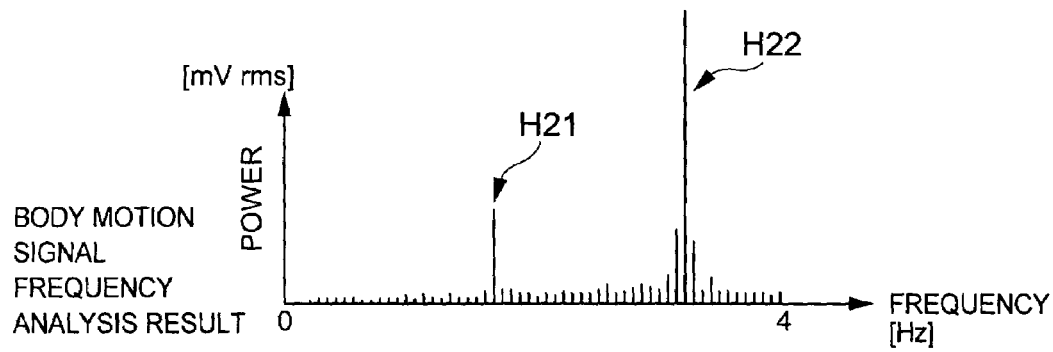
FIG. 7d is a spectrum diagram of the body motion signal of FIG. 7c.

FIG. 7c shows a body motion signal, as might be observed by body motion sensor 302 of FIG. 6. The frequency analysis (i.e. FFT) of this body motion signal is shown in FIG. 7d. As shown, the body motion signal has two spectrum peaks, H21 and H22. These two spectrum peaks H21 and H22 constitute harmonics that affect the flow of blood and thus get combined with (i.e. added to) the pure pulse wave resulting in the observed (i.e. composite) pulse wave of FIG. 7a, which in turn results in the composite spectrum of FIG. 7b.

From direct comparison of the spectrum of FIG. 7b with that of FIG. 7d, it is self-apparent that the first spectrum peak H11 of the observed pulse wave of FIG. 7b (i.e. the composite of the pure pulse wave (not shown) and the pure body motion signal of FIG. 7c) corresponds to the first higher harmonic H21 of the body motion signal, and that the third spectrum peak H12 of the observed pulse wave corresponds to the second higher harmonic H22 of the body motion signal. Since in the present case none of the pure body motion harmonics overlap the pure pulse wave harmonic, elimination of harmonics H11 and H12 from FIG. 7b readily identifies second harmonic H13 as the target harmonic corresponding to the pure pulse wave.

However, determining which of harmonics H11, H12, or H13 to eliminate would not have been so self-apparent if the pure pulse wave harmonic H13 had overlapped either of body motion harmonic H21 or H22. Therefore, the present invention optionally takes an additional step to determine if a body motion harmonic overlaps a harmonic of a pure pulse signal.

First, frequency analysis of the body motion signal is used to identify the higher order harmonics of the body motion signal. These higher harmonics of the body motion signal are then compared with the spectrum of the observed (i.e. composite) pulse wave signal, which will also indicate several spectrum peaks corresponding to its own harmonics. If any of the observed spectrum peaks of the observed pulse wave signal do not coincide with any of the higher harmonics of the body motion signal, then the strongest of the non-coinciding spectrum peaks may be selected for use in calculating the pulse rate.

Optionally, it can additionally be determined if any of the observed spectrum peaks of the observed pulse signal that do coincide with a harmonic of the pure body motion signal include a pure pulse wave component. This would identify any possible higher order pure pulse frequency harmonic that might have been masked by harmonics from the body motion signal.

If all of the spectrum peaks of the observed (i.e. composite) pulse wave coincide with corresponding body motion harmonics, one cannot identify a pure pulse signal harmonic by pure observation (i.e. by the process of elimination described above). In this case, as in the optional case discussed immediately above, it becomes necessary to determine which of the observed spectrum peaks of the composite pulse signal contain a harmonic of the pure pulse wave.

To identify which of the spectrum peaks of the observed pulse wave contain a pure pulse wave harmonic component, the variations in phase shift of the observed spectrum peaks are examined. By determining the amount of phase shift variation in an observed spectrum peak (i.e. harmonic of the observed pulse wave), one can determine if the observed spectrum peak contains a pure pulse wave harmonic component in addition to any body motion harmonic component.

Thus, it is necessary to establish criteria by which the observed variations in phase shift of a harmonic peak of an observed (i.e. composite) pulse wave can be interpreted to determine whether the observed harmonic peak contains any body motion harmonic contribution.

With reference to FIG. 8, various exemplary phase angle variation amounts ($\Delta\sigma$) corresponding to three body motion and pure pulse signal overlapping conditions are shown. In the table of FIG. 8, it is assumed that a pure pulse signal is mixed with a body motion signal that has two harmonics; i.e. a first higher harmonic and a second higher harmonic. Observed phase angle variations are listed for three conditions: (A) neither of the first nor the second body motion higher harmonics overlap the pure pulse signal harmonic; (B) only the first higher harmonic of the body motion signal overlaps the pure pulse signal harmonic; and (C) only the second higher harmonic of the body motion signal overlaps the pure pulse signal harmonic.

In the table of FIG. 8, the first column defines the overlap conditions between the pure pulse signal and the body motion signal. The second and third columns indicate the amount of maximum phase angle variation observed in the spectrum peaks of the observed, composite signal (i.e. combined pure pulse signal and body motion signal) that correspond to the first and second higher harmonics of the original body motions signal.

In the present example, the first row (condition A) corresponds to the condition where the pure pulse signal harmonic does not overlap either of the first or second higher harmonics of the body motion signal. As shown in the second column of the first row, the harmonic of the composite signal (which combines both the pure pulse signal and the body motion signal) that corresponds to the first higher harmonic of the body motion signal indicated a relatively low phase angle variation of 13.2° (i.e. the phase angle varies by about 13.2° about its norm. Similarly, the third column of the first row shows that the harmonic of the composite signal that corresponds to the second higher harmonic of the body motion signal also experiences a relatively low phase angle variation, this time of about 16.8°.

The amount of phase angle variation, however, greatly increases when the harmonic of the pure pulse signal overlaps one of the first or second higher harmonics of the body motion signal.

A first of these situations is demonstrated in the second row of the table (condition B), which corresponds to the condition where the pure pulse signal harmonic overlaps the first higher harmonic of the body motion signal and does not overlap the second higher harmonic of the body motion signal. As shown in the second column of the second row, the harmonic of the composite signal that corresponds to the first higher harmonic of the body motion signal demonstrates an increased phase angle variation of 62.8° due to the overlap of the harmonic of the pure pulse signal. However, as shown in the third column of the second row, the harmonic of the composite signal that corresponds to the second higher harmonic of the body motion signal maintain its small phase shift variation amount of 16.2°.

The second situations where the harmonic of the pure pulse signal overlaps the second higher harmonic of the body motion signal (and not its first harmonic) is shown in the third row of the table (condition C). As shown in the second column of the third row, the harmonic of the composite signal that corresponds to the first higher harmonic of the body motion signal demonstrates only a small phase angle variation value of about 12.9°. However, as shown in the third column of the third row, the harmonic of the composite signal that corresponds to the second higher harmonic of the body motion signal demonstrates an increased phase angle variation of 46.2° due to the overlap of the harmonic of the pure pulse signal with the second harmonic of the body motion signal.

Thus, the present invention can determine if a harmonic of the composite signal consists of an overlapping pure pulse signal harmonic and a body motion signal harmonic by observing the amount of phase angle variation of the composite signal's harmonic. If the amount of phase angle variation is large (i.e. greater than about 30°, or much beyond the margin of error of the phase measuring component), then it is assumed that the harmonic being observed includes a harmonic of the pure pulse signal.

FIG. 9 is an explanatory diagram showing measurement results of temporal changes in the phase angles of first harmonic H11 and third harmonic H12 obtained when the pure pulse wave signal does not overlap either of the first higher harmonic H21 or the second higher harmonic H22 of the body motion signal. As shown, the second higher harmonic H12 has a phase angle variation $\Delta\sigma$ of about 13.2° about its center phase angle, as indicated in FIG. 8. Similarly, the first higher harmonic H11 has a phase angle variation $\Delta\sigma$ of about 16.8° about its center phase angle, as indicated in FIG. 8.

As shown in FIG. 8 and FIG. 9, if the frequency components of the body motion signal and the pure pulse wave signal do not overlap each other, then a variation ($\Delta\sigma$) in the phase angle of the composite signal component H11 that corresponds to the first higher harmonic component H21 of the body motion signal is 13.2°, and the variation ($\Delta\sigma$) in the phase angle of the composite signal component H12 that corresponds to the second higher harmonic component H22 of the body motion signal is 16.8°. This indicates that the variations in the phase angle are not very large. In other words, it may be concluded that the variations are approximately the same level as that of the phase angle variations observed when the errors in various types of measurements of the body motion signal alone are taken into account, assuming that no pulse wave signals exist. That is, the phase variations are within the margin of error of the measuring equipment.

On the other hand, if the pure pulse wave signal overlaps at least either of the first higher harmonic or the second higher harmonic of the body motion signal, then the phase angle variations in the higher harmonic component of the body motion signal are larger than those observed if the pure pulse wave signal does not overlap. This will be described more specifically, below.

FIGS. 10a to 10d correspond to case B of FIG. 8.

Figure 10A:
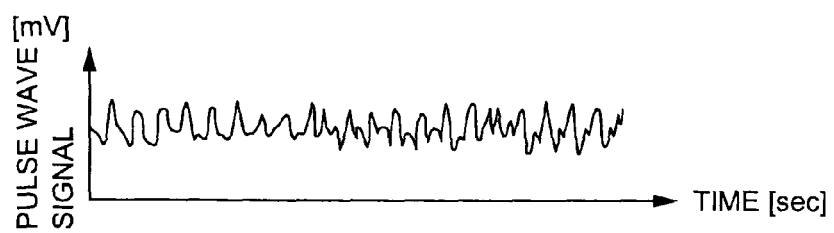
FIG. 10a is a second exemplary diagram of composite (i.e. observed) pulse wave signal.

In FIG. 10a, a second exemplary, observed (i.e. composite) pulse wave is shown. Similarly 10c shows a second exemplary body motion signal. A frequency analysis (i.e. Fast Fourier Transform, FFT, analysis) of the body motion signal of FIG. 10c is shown in FIG. 10d. As shown in FIG. 10d, the body motion signal has a first spectrum peak H21' identifying a first higher harmonic, and has a second spectrum peak H22' identifying a second higher harmonic.

Figure 10B:
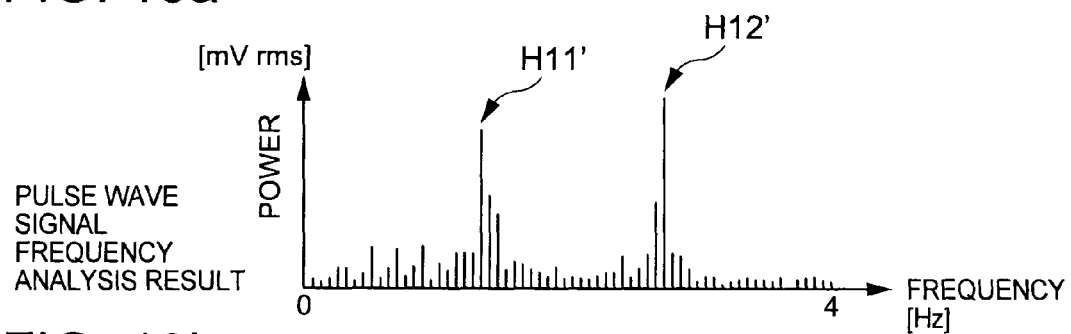
FIG. 10b is a frequency spectrum diagram of the pulse wave of FIG. 10a, showing that the frequency component of the pure pulse wave overlaps one of the two frequency harmonics of the motion signal of FIG. 10d.
Figure 10C:
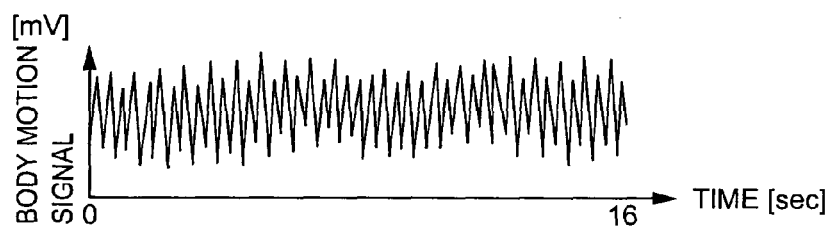
FIG. 10c is a second exemplary diagram of a body motion signal.
Figure 10D:
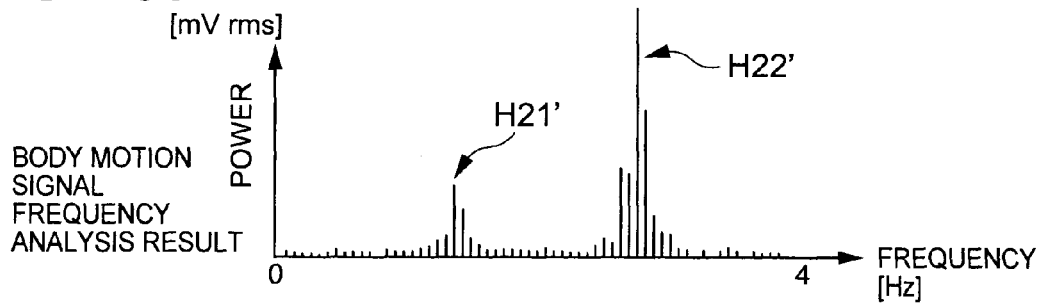
FIG. 10d is a FFT frequency spectrum of the body motion signal of FIG. 10c.

As shown in FIG. 10b, the frequency analysis of the observed pulse wave signal of FIG. 10a reveals the appearance of a first spectrum peak H11' that corresponds to the first higher harmonic H21' of the body motion signal, and reveals a second spectrum peak H12' that corresponds to the second higher harmonic H22' of the body motion signal.

Since only two spectrum peaks H11' and H12' are observed, it can be concluded that the harmonic peak of the pure pulse signal must overlap one of the first H21' or second H22' harmonic peaks of the body motion signal. Therefore, knowledge of the phase angle variations of harmonic peaks H11' and H12' is necessary to determined which harmonic peak includes the pure pulse signal harmonic. In the present example, it will be assumed that the pure pulse wave harmonic overlaps the first harmonic peak H21' of the body motion signal, as explained below.

Figure 11:
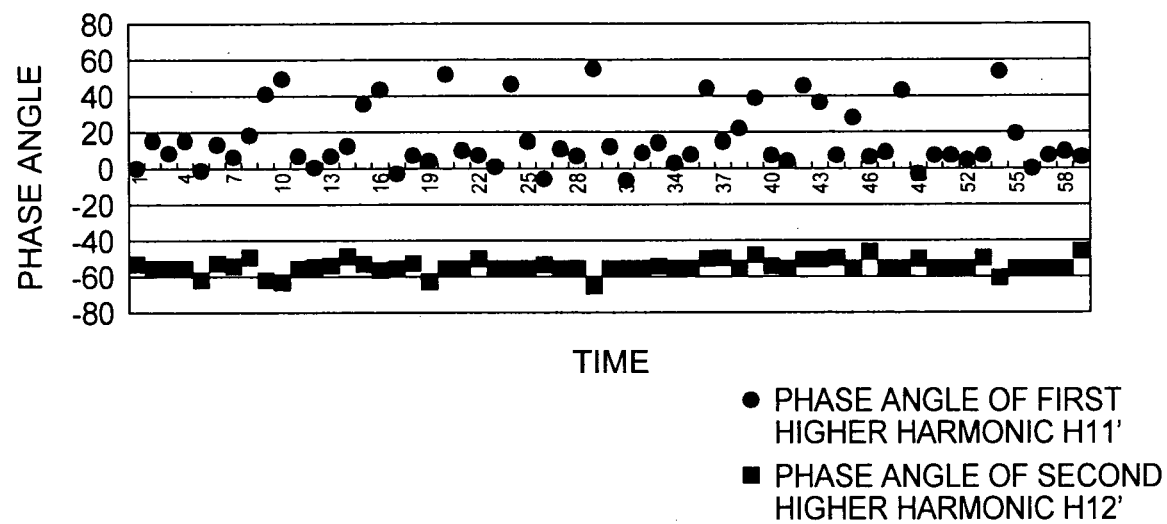
FIG. 11 is an explanatory diagram showing temporal changes in phase angle when the harmonic of the pure pulse wave signal overlaps the first higher harmonic of the body motion signal.

FIG. 11 is an explanatory diagram showing measurement results of temporal changes in the phase angles obtained for harmonic peaks H11' and H12'. The second higher harmonic H12' is shown to still have a small phase angle variation about its center phase angle. However, the first higher harmonic H11' now has an angle variation of about 60°. To determine the significance of this, one needs to compare these findings with the reference information in the table of FIG. 8.

As shown in case B of FIG. 8, when the pure pulse wave signal overlaps the first higher harmonic of the body motion signal (and the pure pulse wave signal does not overlap the second higher harmonic of the body motion signal), the phase angle variation of the first higher harmonic peak of the observed composite pulse signal experiences a large phase angle variation ($\Delta\sigma$) of 62.8°. As also shown in FIG. 8, when the pure pulse wave signal does not overlap the second higher harmonic peak H22' of the body motion signal, the phase angle variation ($\Delta\sigma$) of the second higher harmonic peak H12' was remains relatively low at about 16.2°.

These two conditions agree with the observed phase angle variations shown in FIG. 11 so that it can be concluded that the harmonic peak of the pure pulse signal overlaps the first harmonic peak H21' of the body motion signal.

In other words, if the phase angle variation of the observed pulse wave signal is larger than that in the case where the frequency components of a body motion signal and a pure pulse wave signal do not overlap each other, then it can be concluded that the harmonic peak of the observed pulse signal includes a pulse wave component. This makes it possible to calculate a pulse rate from the harmonic component's corresponding frequency and to display the calculated pulse rate.

Referring now to the processing flowcharts shown in FIG. 12 and FIG. 13, the operation of the embodiment will be explained.

Figure 12:
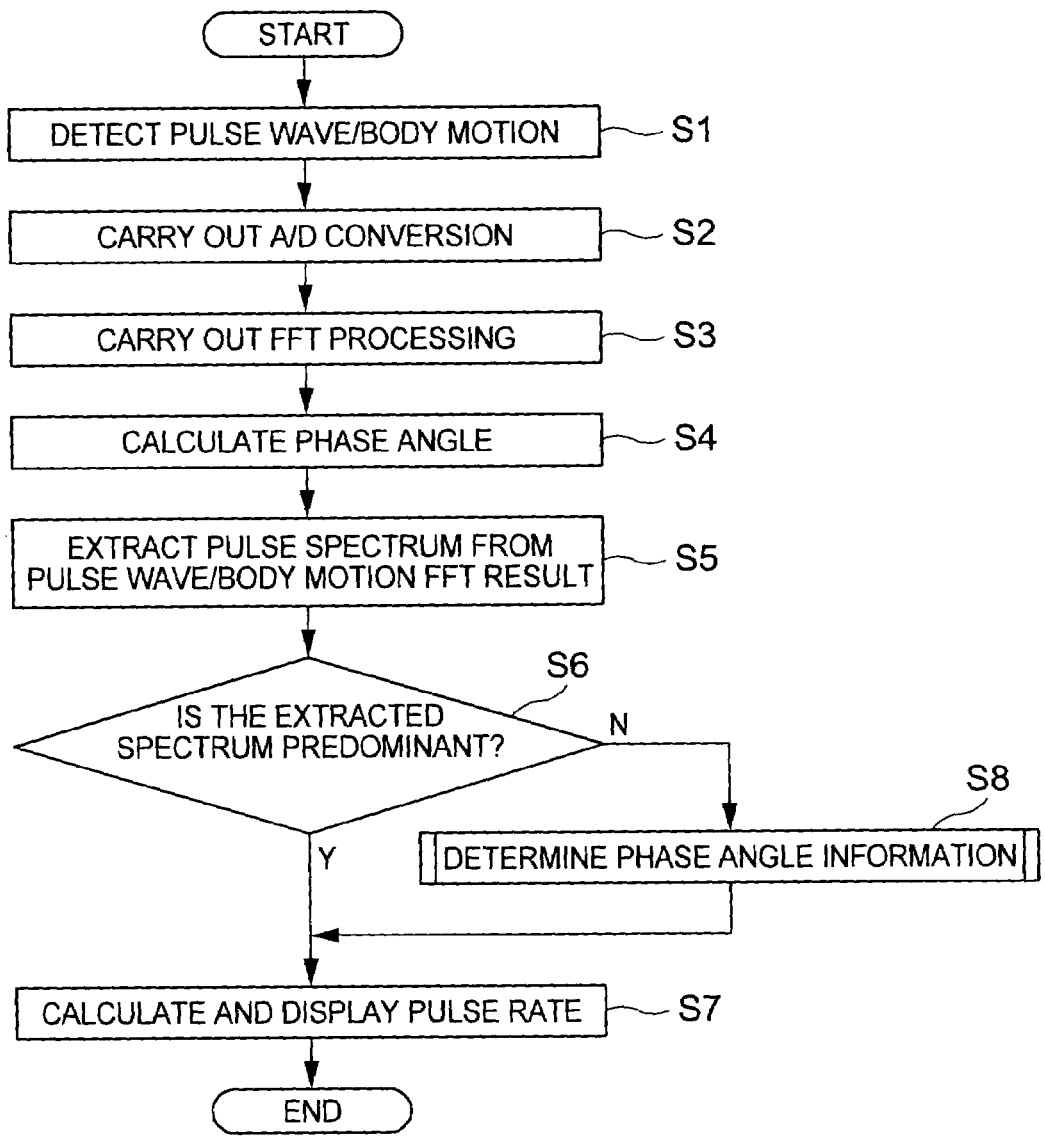
FIG. 12 is a processing flowchart for calculating and displaying a pulse rate.

FIG. 12 is a processing flowchart for calculating and displaying a pulse rate.

First, the wristwatch information device 1 detects a pulse wave and a body motion (step S1).

Specifically with reference to FIG. 6, the pulse wave sensor 30 detects (i.e. observes) the pulse wave from the living body, and outputs the detected pulse wave signal to pulse wave signal amplifier circuit 303.

The pulse wave signal amplifier circuit 303 amplifies the input pulse wave signal and outputs the amplified pulse wave signal to A/D converter 305 and to pulse wave waveform shaping circuit 306.

The pulse wave waveform shaping circuit 306 shapes the pulse wave signal and outputs the shaped signal to the MPU 308.

Meanwhile, the body motion sensor 302 detects the motion of the living body, and outputs the detected body motion signal to body motion signal amplifier circuit 304.

The body motion signal amplifier circuit 304 amplifies the body motion signal and outputs the amplified signal to A/D converter 305 and to body motion waveform shaping circuit 307. The body motion waveform shaping circuit 307 shapes the body motion signal and outputs the shaped signal to the MPU 308.

Then, A/D converter 305 converts the analog pulse wave signal and the analog body motion signal into respective digital representations, and outputs the converted signals as pulse wave data and body motion data, respectively, to MPU 308 (step S2).

Subsequently, MPU 308 carries out fast Fourier transformation (FFT) processing on the received pulse wave data and body motion data (step S3).

Subsequently, MPU 308 performs phase angle calculation processing (step S4).

Furthermore, MPU 308 extracts a pulse spectrum from the result of the FFT processing on the pulse wave data and the body motion data (step S5).

Specifically, when the observed pulse wave spectrum is denoted as fmg, the body motion spectrum is denoted as fsg, and a pulse wave component is denoted as fM, the processing shown below is carried out:

$$fM = fmg - fsg$$

This means that the frequency component of the pure pulse wave signal is taken out (i.e. included in the extracted pulse wave component fM).

Then, the largest frequency component in the extracted pulse wave component fM is defined as a spectrum peak corresponding to the pure pulse signal.

Subsequently, the MPU 308 determines whether the extracted spectrum peak is predominant (step S6). The extracted spectrum (the largest frequency spectrum peak in a pulse wave component fM) is determined to be predominant if the extracted spectrum peak has a height that is double or more that of a tenth highest frequency spectrum peak among the frequency spectrum peaks included in the output of the pulse wave sensor 30.

If it is determined in step S6 that the extracted spectrum peak is not predominant (No in step S6), that is, if no predominant spectrum peak is detected, then the MPU 308 proceeds to phase angle information determination processing (step S8).

Figure 13:
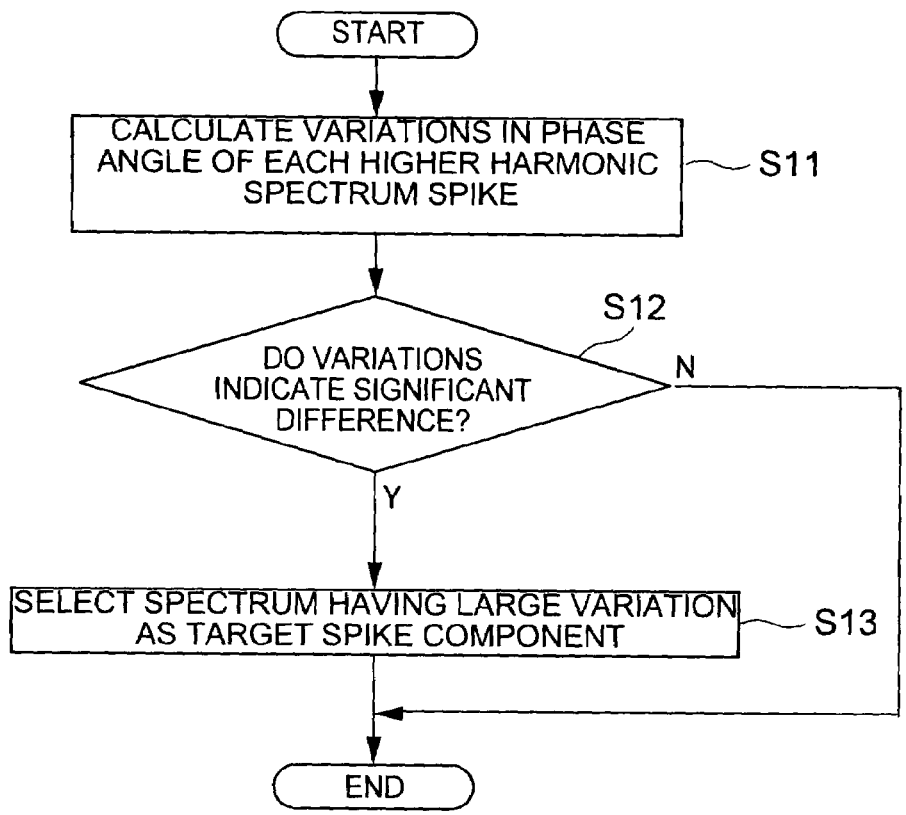
FIG. 13 is a processing flowchart for phase angle information determination processing according to a first embodiment.

FIG. 13 is a processing flowchart of the phase angle information determination processing according to the first embodiment.

First, MPU 308 calculates the phase angle variation per unit time of each higher harmonic spectrum peaks (step S11) extracted from the pulse wave component fM.

Subsequently, MPU 308 determines whether the phase angle variations have a significant difference (step S12), as discussed above in reference to FIG. 8.

If it is determined in step S12 that the variations have a significant difference (Yes in step S12), then MPU 308 identifies the spectrum peak having the largest phase angle variation as the target spectrum peak (step S13) that includes a higher harmonic component of the pure pulse wave, and proceeds to step S7.

If it is determined in step S12 that the variations have no significant difference (No in step S12), then MPU 308 directly proceeds to step S7.

If it is an extracted spectrum peak is identified as predominant in step S6 (Yes in step S6), then the MPU 308 proceeds to step S7.

The MPU 308 then calculates a pulse rate from the frequency of the spectrum peak identified as corresponding to a higher harmonic of the pure pulse wave (i.e. the harmonic component determined to be predominant in step S6 or the spectrum peak identified as the spectrum peak having the largest phase angle variation in step S13), and displays the calculated pulse rate on the display unit (step S7).

As described above, according to the first embodiment, the pulse detection accuracy can be improved by utilizing the variations in phase angle even when a significant result cannot be obtained merely by determining the difference between the pulse wave spectra fmg and the body motion spectra fsg to simply calculate the pulse wave component fM.

The pulse rate detection accuracy will be improved especially as compared to the situation when the pure pulse rate signal and the body motion signal frequency during walking are close.

[2] Second Embodiment

In the first embodiment, when the frequency component derived from a observed pulse wave and the frequency component derived from a body motion wave share a proximate dominant frequency, the higher harmonic spectrum peak having the largest variation in phase angle is identified as the target spectrum component from which to extract the frequency component of the pure pulse wave. In this second embodiment, a phase angle difference between the phase angles of the higher harmonic spectrum peaks of an observed pulse wave signal and the phase angles of the higher harmonic spectrum peaks of a body motion signal corresponding to the higher harmonics of the observed pulse wave signal is determined. Then, a higher harmonic spectrum peak exhibiting the largest variation per unit time in the phase angle difference is identified as the target spectrum component, i.e. as the frequency component containing pure pulse wave information.

The second embodiment differs from the first embodiment only in the phase angle information determination processing step (refer to step S8 in FIG. 12). Hence, the descriptions will be given primarily of the aspects different from the first embodiment.

The MPU 308 determines whether an extracted spectrum peak is predominant (step S6 in FIG. 12), and if the extracted spectrum peak is not predominant (No in step S6), that is, if no predominant spectrum peak is detected, then the MPU 308 proceeds to phase angle information determination processing (step S8).

Figure 14:
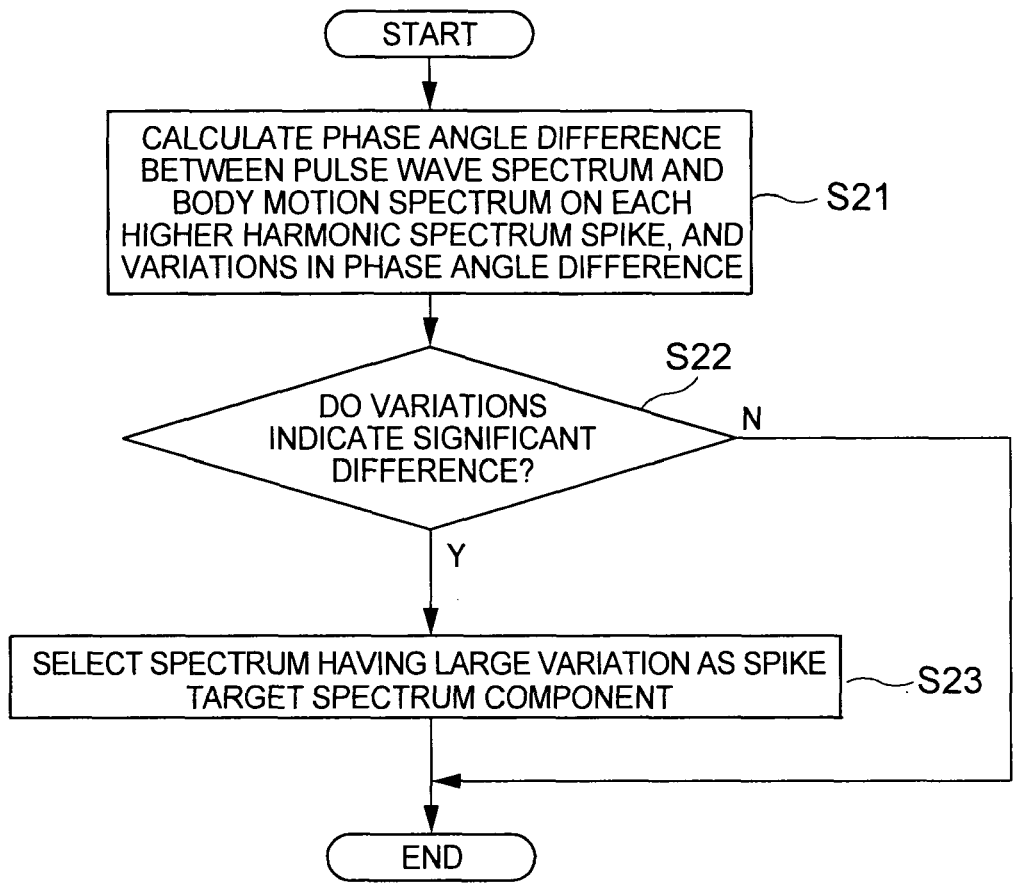
FIG. 14 is a processing flowchart for phase angle information determination processing according to a second embodiment.

FIG. 14 is a flowchart of the phase angle information determination processing (step S8 in FIG. 12) of the second embodiment.

First, the MPU 308 calculates the phase angle difference between a pulse wave spectrum and a corresponding body motion spectrum for each higher harmonic spectrum peak, then calculates the variations in the phase angle difference per unit time (step S21).

Subsequently, the MPU 308 determines whether the variations in the phase angle difference per unit time of each higher harmonic spectrum peak show a significant difference (step S22). A significant difference may be defined as a difference that is higher than the expected margin of error of the phase angle calculating equipment. Alternatively, a difference of at least 30° may be used as the indicator of a "significant difference".

If the determination result in step S22 indicates that the variations in phase angle difference per unit time show a significant difference (Yes in step S22), then the MPU 308 selects the spectrum peak exhibiting the largest variation in phase angle difference per unit time as the target spectrum peak (step S23), and proceeds to step S7.

If the determination result in step S22 indicates no significant difference in the variations in phase angle difference per unit time (No in step S22), then the MPU 308 directly proceeds to step S7 of FIG. 12.

If the determination result in step S6 indicates that the extracted spectrum peak is predominant (Yes in step S6), the MPU 308 proceeds to step S7.

Then, the MPU 308 calculates a pulse rate from the frequency of the target spectrum peak determined to be predominant in step S6 or the spectrum peak selected as the spectrum exhibiting the largest variation in phase angle in step S13, and displays the calculated pulse rate on a display device (step S7).

Thus, as compared with the first embodiment, in which the variations in phase angle are utilized, the second embodiment makes it possible to further improve the pulse detection accuracy by utilizing the variations in phase angle difference per unit time even when a significant difference cannot be obtained merely by determining the difference between the pulse wave spectra fmg and the body motion spectra fsg to simply calculate the pulse wave component fM.

[3] Modification Examples of the Embodiments

In the above descriptions, it has been assumed that pulse wave spectra include body motion spectra; however, the same descriptions can be applied also to a case where body motion spectra include pulse wave spectra.

In the above descriptions, both body motion spectra and pure pulse wave spectra have been detected.

In the above descriptions, the control program has been stored beforehand in the ROM 310 of the controller 5. Alternatively, however, the control programs may be recorded beforehand in recording media, such as various types of magnetic disks, optical disks, or memory cards, so that the control programs may be read from these recording media and installed.

It is also possible to download the control programs via a network, such as the Internet or a LAN, and install the downloaded control programs so as to execute them.

ADVANTAGES

According to the present invention, to extract a pulse wave component from the results of frequency analyses of a pulse wave sensor and a body motion sensor, respectively, even if a spectrum corresponding to the pulse wave component and a higher harmonic spectrum corresponding to a body motion component appear at a location close to each other frequency-wise, the spectrum corresponding to the pulse wave component can be easily identified. Thus, the accuracy of pulse detection can be improved.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A pulsimeter comprising:
    a pulse wave detector that has a pulse wave sensor and outputs a pulse wave signal;
    a frequency analyzer for carrying out a frequency analysis on the pulse wave signal;
    a candidate extractor for extracting candidate spectrum peaks based on the frequency analysis result of the frequency analyzer;
    a phase angle information detector for detecting phase angle information of each of the extracted candidate spectrum peaks;
    a spectrum peak selector for selecting a target spectrum peak for calculating a pulse rate from among the extracted candidate spectrum peaks based on their respective phase angle information; and
    a pulse rate calculator for calculating the pulse rate based on the target spectrum peak.

2. The pulsimeter according to claim 1, wherein
    the phase angle information includes at least one of information regarding variations in phase angle and variations in phase angle difference per unit time; and
    the spectrum peak selector selects as the target spectrum peak the candidate spectrum peak exhibiting the greatest variation in phase angle or the greatest variation in phase angle difference per unit time.

3. A pulsimeter comprising:
    a pulse wave detector that has a pulse wave sensor and outputs a pulse wave signal;
    a body motion detector that has a body motion sensor and outputs a body motion signal;
    a frequency analyzer for carrying out a frequency analysis on each of the pulse wave signal and the body motion signal;
    a preliminary extractor for extracting preliminary spectrum peaks of the pulse wave signal and the body motion signal based on the frequency analysis result of the frequency analyzer;
    a candidate extractor for extracting candidate spectrum peaks by taking the difference of the preliminary spectrum peaks of the pulse wave signal and the body motion signal;
    a target spectrum peak selector for identifying as higher magnitude spectrum peaks any candidate spectrum peak greater than a predefined reference amount, and for selecting as a target spectrum peak the highest of the identified higher magnitude spectrum peaks;
    a phase angle information detector for determining phase angle information, of the extracted candidate spectrum peaks if the target spectrum peak selector identifies no higher magnitude spectrum peaks;
    wherein said target spectrum peak selector selects said target spectrum peak among the candidate spectrum peaks based on the phase angle information if no higher magnitude spectrum peaks are identified; and
    a pulse rate calculator for calculating a pulse rate on the basis of said target spectrum peak.

4. The pulsimeter according to claim 3, wherein said target spectrum peak selector includes a first peak selector and a second peak selector;
    said first peak selector being effective selecting as said target spectrum peak the highest of the identified higher magnitude spectrum peaks; and
    said second peak selector being effective for selecting said target spectrum peak from among the candidate spectrum peaks based on the phase angle information if no higher magnitude spectrum peaks are identified.

5. The pulsimeter according to claim 3, wherein
    the phase angle information includes information regarding variations in phase angle or variations in phase angle difference per unit time; and
    the target spectrum peak selector selects as the target spectrum peak the candidate spectrum peak exhibiting the greatest variation in phase angle or the greatest variation in phase angle difference per unit time.

6. A control method for a pulsimeter provided with a pulse wave detector that has a pulse wave sensor and outputs a pulse wave signal, comprising:
    a frequency analysis step for carrying out a frequency analysis on the pulse wave signal;
    a candidate extraction step for extracting candidate spectrum peaks based on the result of the frequency analysis;
    a phase angle information detection step for detecting phase angle information for each of the extracted candidate spectrum peaks;
    a spectrum peak selection step for selecting a target spectrum peak for calculating a pulse rate from among the extracted candidate spectrum peaks based on their respective phase angle information; and
    a pulse rate calculation step for calculating a pulse rate based on the target spectrum peak.

7. The control method for a pulsimeter according to claim 6, wherein
    the phase angle information includes at least one of information regarding variations in phase angle and variations in phase angle difference per unit time; and
    the spectrum peak selection step selects as the target spectrum peak the candidate spectrum peak exhibiting the greatest variation in phase angle or the greatest variation in phase angle difference per unit time.

8. A control method for a pulsimeter provided with a pulse wave detector that has a pulse wave sensor and outputs a pulse wave signal and a body motion detector that has a body motion sensor and outputs a body motion signal, comprising:
    a frequency analysis step for carrying out a frequency analysis on each of the pulse wave signal and the body motion signal;
    a preliminary extraction step for extracting preliminary spectrum peaks of the pulse wave signal and the body motion signal based on the result of the frequency analysis;
    a candidate identification step for identifying candidate spectrum peaks by taking the difference of the preliminary spectrum peaks of the pulse wave signal and the body motion signal, and for identifying as higher magnitude spectrum peaks any candidate spectrum peak greater than a predefined reference amount;

a phase angle information detection step for determining phase angle information of extracted candidate spectrum peaks if no higher magnitude spectrum peaks are identified;

a target spectrum peak selection step for selecting a target spectrum peak, wherein the highest of the identified higher magnitude spectrum peaks is selected as said target spectrum peak or if no higher magnitude spectrum peaks are identified then the target spectrum peak is selected from among the candidate spectrum peaks based on their phase angle information; and a pulse rate calculation step for calculating a pulse rate based on the target spectrum peak.

9. The control method for a pulsimeter according to claim 8, wherein said target spectrum peak includes a first peak selection sub-step and a second peak selection sub-step;

wherein said first peak selection sub-step includes selecting the highest of the identified higher magnitude spectrum peaks as said target spectrum peak; and wherein said second peak selection sub-step includes selecting the target spectrum peak from among the candidate spectrum peaks based on their phase angle information if no higher magnitude spectrum peaks are identified.

10. The control method for a pulsimeter according to claim 8, wherein said phase angle information detection step is skipped if higher magnitude spectrum peaks are identified in said candidate identification step.

11. The control method for a pulsimeter according to claim 8, wherein the phase angle information includes information regarding variations in phase angle or variations in phase angle difference per unit time ; and the target spectrum peak selection step selects as said target spectrum peak the candidate spectrum peak exhibiting the greatest variation in phase angle or the greatest variation in phase angle difference per unit time if no higher magnitude spectrum peaks are identified.

12. A wristwatch information device comprising:
a pulse wave detector that has a pulse wave sensor and outputs a pulse wave signal; and
a main unit for attachment to an arm of a body, wherein the main unit includes:
  a frequency analyzer for carrying out a frequency analysis on the pulse wave signal;
  a candidate extractor for extracting candidate spectrum peaks based on the frequency analysis result of the frequency analyzer;
  a phase angle information detector for detecting phase angle information of each of the extracted candidate spectrum peaks;
  a spectrum peak selector for selecting a target spectrum peak for calculating a pulse rate from among the extracted candidate spectrum peaks based on their respective phase angle information;
  a pulse rate calculator for calculating the pulse rate based on the target spectrum peak; and
  a display unit for displaying the calculated pulse rate.

13. A wristwatch information device, comprising:
a pulse wave detector that has a pulse wave sensor and outputs a pulse wave signal; and
a main unit for attachment to an arm of a body, wherein the main unit includes:
  a body motion detector that has a body motion sensor and outputs a body motion signal;
  a frequency analyzer for carrying out a frequency analysis on each of the pulse wave signal and the body motion signal;
  a preliminary extractor for extracting preliminary spectrum peaks of the pulse wave signal and the body motion signal based on the frequency analysis result of the frequency analyzer;
  a candidate extractor for extracting candidate spectrum peaks by taking the difference of preliminary spectrum peaks of the pulse wave signal and the body motion signal spectra;
  a target spectrum peak selector for identifying as higher magnitude spectrum peaks any candidate spectrum peak greater than a predefined reference amount, and for selecting as a target spectrum peak the highest of the identified higher magnitude spectrum peaks;
  a phase angle information detector for determining phase angle information of the extracted candidate spectrum peaks if the target spectrum peak selector identifies no higher magnitude spectrum peaks;
  wherein said target spectrum peak selector selects said target spectrum peak from among the candidate spectrum peaks based on the phase angle information if no higher magnitude spectrum peaks are identified;
  a pulse rate calculator for calculating a pulse rate on the basis of said target spectrum peak; and
  a display unit for displaying the calculated pulse rate.

14. The wristwatch information device of claim 13, wherein said spectrum peak selector includes a first target peak selector and a second target peak selector;

said first target peak selector being effective for selecting as said target spectrum peak the highest of the identified higher magnitude spectrum peaks;

said second target peak selector being effective for selecting said target spectrum peak from among the candidate spectrum peaks based on the phase angle information if no higher magnitude spectrum peaks are identified.

15. A control program for controlling, by a computing device, a pulsimeter equipped with a pulse wave detector that has a pulse wave sensor and outputs a pulse wave signal, said control program causing:

frequency analysis on the pulse wave signal;
extraction of candidate spectrum peaks based on the result of the frequency analysis;
detection of phase angle informationfor each of the extracted candidate spectrum peaks;
selection of a target spectrum peak for calculating a pulse rate from among the candidate spectrum peaks based on the phase angle information; and
calculation of a pulse rate based on the target spectrum peak.

16. A computer-readable recording medium in which the control program of claim 15 is recorded.

17. A control program for controlling, by a computing device, a pulsimeter provided with a pulse wave detector that has a pulse wave sensor and outputs a pulse wave signal and a body motion detector that has a body motion sensor and outputs a body motion signal; said control program causing:

frequency analysis on each of the pulse wave signal and the body motion signal;
extraction of preliminary spectrum peaks corresponding to the pulse wave signal and the body motion signal based on the result of the frequency analysis;
identification of candidate spectrum peaks by taking the difference of the preliminary spectrum peaks of the pulse wave signal and the body motion signal and identifying as higher magnitude spectrum peaks any candidate spectrum peaks greater than a predefined reference amount;

determination of phase angle information for the extracted candidate spectrum peaks if no higher magnitude spectrum peaks are identified;

selection of a target spectrum peak, wherein the highest of the identified higher magnitude spectrum peaks is selected as said target spectrum peak or if no higher magnitude spectrum peaks are identified then the target spectrum peak is selected from among the candidate spectrum peaks based on their phase angle information; and calculation of a pulse rate on the basis of the target spectrum peak.

18. A computer-readable recording medium in which the control program of claim 17 is recorded.

* * * * *